(12) United States Patent
Klimasauskas et al.

(10) Patent No.: US 8,889,352 B2
(45) Date of Patent: *Nov. 18, 2014

(54) CONVERSION OF ALPHA-HYDROXYALKYLATED RESIDUES IN BIOMOLECULES USING METHYLTRANSFERASES

(75) Inventors: Saulius Klimasauskas, Vilnius (LT); Zita Liutkeviciute, Vilnius (LT); Edita Kriukiene, Vilnius (LT)

(73) Assignee: Vilnius University, Vilnius (LT)

( * ) Notice: Subject to any disclaimer, the term of this patent is extended or adjusted under 35 U.S.C. 154(b) by 157 days.

This patent is subject to a terminal disclaimer.

(21) Appl. No.: 13/262,738

(22) PCT Filed: Apr. 1, 2010

(86) PCT No.: PCT/EP2010/054437
§ 371 (c)(1),
(2), (4) Date: Dec. 19, 2011

(87) PCT Pub. No.: WO2010/115847
PCT Pub. Date: Oct. 14, 2010

(65) Prior Publication Data
US 2012/0088238 A1    Apr. 12, 2012

(30) Foreign Application Priority Data

Apr. 2, 2009   (LT) .................................. 2009 023
May 8, 2009   (LT) .................................. 2009 032

(51) Int. Cl.
*C12Q 1/68*      (2006.01)
*C07H 21/02*    (2006.01)
*B01L 3/00*      (2006.01)
*C12P 19/34*    (2006.01)

(52) U.S. Cl.
USPC ......... 435/6.1; 435/91.1; 536/23.1; 536/24.1; 422/430

(58) Field of Classification Search
USPC .......... 536/23.1, 24.1; 435/6.1, 91.1; 422/430
See application file for complete search history.

(56) References Cited

U.S. PATENT DOCUMENTS

2007/0161007 A1    7/2007   Rajski et al.

FOREIGN PATENT DOCUMENTS

WO    WO 2010/115847    10/2010

OTHER PUBLICATIONS

Bird, (2002), "DNA Methylation Patterns and Epigenetic Memory," Genes Dev. 16, 6-21.
Bong and Ghaderi, (2001), "Chemoselective Pd(0)-Catalyzed Peptide Coupling in Water," Org. Lett. 3, 2509-2511.
Casalnuovo and Calabrese, (1990), "Palladium-Catalyzed Alkylations in Aqueous Media," J. Am. Chem. Soc. 112, 4324-4330.
Cheng, (1995), "Structure and Function of DNA Methyltransferase," Annu. Rev. Biophys. Biomol. Struct. 24, 293-318.

(Continued)

*Primary Examiner* — Jezia Riley
(74) *Attorney, Agent, or Firm* — Thompson Hine LLP (57) ABSTRACT

The present invention relates to targeted conversion of alpha-hydroxyalkylated residues in biomolecules in the presence of a directing methyltransferase, namely to targeted removal of the alpha-hydroxyalkyl moieties to give unmodified residues, or targeted derivatization of the alpha-hydroxyalkyl groups by covalent coupling of non-cofactor compounds represented by formula HQ-LX1 wherein X represents a functional group or a reporter group attached via a linker moiety L, and QH is selected from HS—, HSe—, HO—H$_2$N—, HN$_3$ or HCN in the presence of a directing methyltransferase. Further development of the method of targeted conversion comprises methods for targeted labeling a biomolecule and method for detecting hydroxymethylated target sites in a biomolecule according to the present invention.

11 Claims, 6 Drawing Sheets

(56) References Cited

OTHER PUBLICATIONS

Dawson et al., (1994), "Synthesis of Proteins by Native Chemical Ligation," Science 266, 776-779.
DeVasher et al., (2004), "Aqueous-Phase, Palladium-Catalyzed Cross-Coupling of Aryl Bromides under Mild Conditions, Using Water-Soluble, Sterically Demanding Alkylphosphines," J. Org. Chem. 69, 7919-7927.
Dibowski and Schmidtchen, (1998), "Bioconjugation of Peptides by Palladium-Catalyzed C-C Cross-Coupling in Water," Angew. Chem. Int. Ed. 37, 476-478.
Djuric, Z. et al. (1996), "Levels of 5-Hydroxymethyl-2'-Deoxyuridine in DNA from Blood as a Marker of Breast Cancer," Cancer 77, 691-696.
Frommer et al. (1992), "A genomic sequencing protocol that yields a positive display of 5-methylcytosine residues in individual DNA strands," Proc Natl Acad Sci USA 89, 1827-1831.
Gieselman et al. (2002), "Selenocysteine Derivatives for Chemoselective Ligations," ChemBioChem 3, 709-716.
Goll, "Eurkaryotic Cystosine Methyltransferases," M.G. & Bestor, T.H. Annu. Rev. Biochem. 74, 481-514 (2005).
Gommers-Ampt, J.H. & Borst, P. (1995), "Hypermodified bases in DNA," FASEB J. 9, 1034-1042.
Graham et al., (2002), "Internal Labeling of Oligonucleotide Probes by Diels-Alder Cycloaddition," Tet. Lett. 43, 4785-4788.
Kriaucionis, S. & Heintz, N. (2009), "The Nuclear DNA Base 5-Hydroxymethylcytosine is Present in Purkinje Neurons and the Brain," Science 324, 929-930.
Lewis et al. (2002), "Click Chemistry In Situ: Acetylcholinesterase as a Reaction Vessel for the Selective Assembly of a Femtomolar Inhibitor from an Array of Building Blocks," Angew. Chem. Int. Ed. 41, 1053-1057.
Liu and Tam, (1994) "Peptide segment ligation strategy without use of protecting groups," Proc. Natl. Acad. Sci. USA 91, 6584-6588.
Penn et al., (1972), "The Presence of 5-Hydroxymethylcytosine in Animal Deoxyribonucleic Acid," Biochem. J. 126, 781-790.
Saxon and Bertozzi, (2000), "Cell Surface Engineering by a Modified Staudinger Reaction," Science 287, 2007-2010.
Schumacher et al., (2006), "Microarray-based DNA methylation profiling: technology and applications," Nucleic Acids Res. 34, 528-542.
Tahiliani, M. et al., "Conversion of 5-Methylcytosine to 5-Hydroxymethylcytosine in Mammalian DNA by MLL Partner TET1," Science 324, 930-935.
Valinluck, V. et al., (2004), "Oxidative damage to methyl-CpG sequences inhibits the binding of the methyl-CpG binding domain (MBD) of methyl-CpG binding protein 2 (MeCP2)," Nucleic Acids Res. 32, 4100-4108.
Wong et al., (2005), "Phenotypic differences in genetically identical organisms: the epigenetic perspective," Hum Mol Genet 14, R11-R18.
Wirth, T. (2000), "Organoselenium Chemistry in Stereoselective Reactions," Angew. Chem. Int. Ed. 39, 3741-3749.
Zelakiewicz et al., "Observation of Selenium-77 Nuclear Magnetic Resonances in Octaneselenol-Protected Gold Nanoparticles," J. Am. Chem. Soc., 2004, 126, 8112-8113.
PCT, International Search Report, International Application No. PCT/EP2010/054437 (mailed Jul. 19, 2010, published Oct. 14, 2010).
User Guide entitled "EpiQuik™ DNA Methyltransferase Activity/Inhibition Assay Kit," Catalog No. P-3001, Version 3.1006, epigentek.com/docs/P-3001.pdf (Jan. 25, 2008).
Roll, J.D. et al., "DNMT3b overexpression contributes to a hypermethylator phenotype in human breast cancer cell lines," *Molecular Cancer*, Biomed Central, vol. 7, No. 1 (Jan. 25, 2008).
Hayatsu, H. et al., "Reaction of Bisulfite with the 5-Hydroxymethyl Group in Pyrimidines and in Phage DNAs," *Biochemistry*, vol. 18, No. 4, p. 632-637 (1979).
Grafstrom, R.C. et al., Pathobiological effects of acetaldehyde in cultured human epithelial cells and fibroblasts, *Carcinogenesis*, vol. 15, No. 5, pp. 985-990 (1994).
Liukeviciute, Z. et al., Cytosine-5-methyltransferases add aldehydes to DNA, *Nature Chemical Biology*, vol. 5, No. 6, pp. 400-402 (May 10, 2009).
Garman, Non-radioactive labeling: A practical introduction, Biological Techniques Series, Academic Press (1997), pp. 1-132.
Weber et al., Chromosome-wide and promoter-specific analyses identify sites of differential DNA methylation in normal and transformed human cells, Nat Genet vol. 37, No. 8 (2005), pp. 853-862.

CONVERSION OF ALPHA-HYDROXYALKYLATED RESIDUES IN BIOMOLECULES USING METHYLTRANSFERASES

PRIORITY CLAIM

This application is a National Phase of PCT/EP2010/054437 filed Apr. 1, 2010, which claims priority to Lithuanian Patent Application No. LT2009023 filed Apr. 2, 2009 and Lithuanian Patent Application No. LT2009032 filed May 8, 2009.

FIELD OF THE INVENTION

The present invention relates to methyltransferase-directed sequence-specific covalent conversion of alpha-hydroxyalkylated residues in modified biomolecules, namely relates to i) methyltransferase-directed removal of alpha-hydroxyalkyl groups to yield unmodified residues, and ii) methyltransferase-directed derivatization of alpha-hydroxyalkyl groups by coupling non-cofactor nucleophilic compounds in said modified biomolecule.

Namely, this invention covers a method for targeted conversion of alpha-hydroxyalkylated target residues in biomolecules as well as a method for targeted labeling of alpha-hydroxyalkylated target residues in biomolecules, method for detecting alpha-hydroxyalkylated target residues in a biomolecule and a kit for performing the methods mentioned, all grounded on the idea of conversion of alpha-hydroxyalkylated target residues using a cofactor-free directing methyltransferase.

The present invention is exemplified using DNA methyltransferases (MTases). However, it can also be used with RNA methyltransferases as well as methyltransferases acting on other biomolecules.

In this description the term "methyltransferase" refers to enzymes that normally transfer the methyl from S-adenosyl-L-methionine (AdoMet) onto their substrate. Preferably, the methyltransferase is an enzyme capable of methylating DNA, RNA or (poly)peptides. More preferably, the methyltransferase is a DNA cytosine-5 methyltransferase that uses a covalent activation mechanism for the transfer of the methyl groups on the C5 position of a target cytosine residue. More preferably, the methyltransferase is selected from M.HhaI, M.SssI, M.HpaII or a derivative thereof. The term "M.HhaI" refers to the DNA methyltransferase deposited in the Swissprot database under accession number P05102. All MTases used in this invention are cofactor-free, i.e. MTase preparations contain no more than 2 mol % of bound endogenous cofactor AdoMet.

The term "biomolecule" means DNA, RNA or (poly)peptide. The term "(poly)peptide" refers alternatively to peptide or to polypeptide. Preferably, the biomolecule is chromosomal or genomic DNA. Biomolecules may be entirely natural, i.e. unmodified, synthetic or modified and may exist as complexes. For example the term "nucleic acid molecule" comprises DNA and RNA molecules or RNA/DNA hybrids as well as modified DNA and RNA molecules. DNA may be for example cDNA or genomic DNA. RNA may be for example mRNA, hnRNA, tRNA, rRNA etc.

The term "modified biomolecule" means a biomolecule that contains modified residues. Modified residues are those that contain additional chemical entities (modifying side chains) as compared to normal major components of the biomolecule. DNA normally consists of four major unmodified residues (C, T, A, G); a certain fraction of C and A residues are found to be modified in natural DNA. Such modifications are typically brought about via action of intracellular enzymes (see below).

The term "conversion of a modified residue" means either removal of the modifying moiety to give an unmodified residue, or further derivatization (chemical extension) of that moiety to give a derivatized residue.

The term "removal" means chemical splitting of a compound by breaking a stable covalent bond (such as a C—C or N—C bond) thus yielding an unmodified residue and a small molecule, typically an aldehyde.

The term "derivatization" means extending a biomolecule by coupling of chemical entities, such as carbon chains, chemically reactive groups or reporter groups into biomolecules, such as DNA without otherwise changing the target biomolecule.

The term "coupling" means chemical addition of a compound by making a stable covalent bond (such as a C—C bond, C—O bond, C—S bond, C—Se bond or C—N bond). The coupling reaction can be an addition of an entire exogenous compound to a target biomolecule or its condensation whereby a hydroxyl group in the target biomolecule is replaced with a whole molecule of the exogenous compound with release of a water molecule ($H_2O$).

BACKGROUND OF THE INVENTION

Besides the four major nucleobases (C, A, G and T), DNA of most living organisms contains minor amounts of their methylated variants: 5-methylcytosine (5mC), N4-methylcytosine and N6-methyladenine. These methylated species are formed by DNA methyltransferase enzymes (MTases), which catalyze the transfer of a methyl group from the cofactor S-adenosyl-L-methionine (AdoMet) to form the above methylated nucleotides at specific positions of their target sequences (Cheng, (1995) *Annu. Rev. Biophys. Biomol. Struct.* 24, 293-318). It is well established that DNA methylation is an important biological mechanism that regulates gene expression in vertebrate animals including humans (Bird, A. (2002) *Genes Dev.* 16, 6-21), Goll, M. G. & Bestor, T. H. *Annu. Rev. Biochem.* 74, 481-514 (2005) and serves as a species self-code in bacteria. Genomic DNA sometimes contains 5-hydroxymethylated pyrimidine nucleobases 5-hydroxymethylcytosine and 5-hydroxymethyluracil (hmC and hmU) (Gommers-Ampt, J. H. & Borst, P. (1995) *FASEB J.* 9, 1034-1042).

Glucosylation of the 5-hydroxymethyl groups in certain bacteriophages and an African trypanosome serves to protect the invading genome against host defense systems. The presence of hmC was previously reported in DNA from animal brains (Penn et al., (1972) *Biochem. J.* 126, 781-790). Recent studies of genomic DNA from human neurons and brains (Kriaucionis, S. & Heintz, N. *Science* 324, 929-930), as well as DNA from mouse embryonic stem cells (Tahiliani, M. et al. *Science* 324, 930-935) found that hmC residues occur at CG sequences and that they are likely produced by oxidation of mC residues. The 5-hydroxymethyl groups in DNA may alter interactions with cellular proteins involved in epigenetic control of gene activity (Valinluck, V. et al. (2004) *Nucleic Acids Res.* 32, 4100-4108), whereas elevated levels of hmU in DNA were reported to correlate with incidents of breast cancer (Djuric, Z. et al. (1996) *Cancer* 77, 691-696). Altogether, the above evidence suggests that 5-hydroxymethylate nucleobases, and hmC in particular, may play important roles in embryonic development, brain function and cancer progression. However, neither the chromosomal localization of hmC residues nor the underlying biological mechanisms are currently known, and further studies are required to address these fundamental issues. Most importantly, such studies are hampered by the lack of adequate analytical techniques that would permit facile analysis of hmC residues in DNA.

Current analytical techniques to study cytosine modifications in mammalian DNA are based on the existence of two epigenetic states of cytosine in CG sites: unmodified cytosine (C) and 5-methylated cytosine (5mC). To this end, numerous techniques have been developed for the identification and localization of 5mC in DNA (Schumacher et al. (2006) *Nucleic Acids Res.* 34, 528-542). The gold standard method to study the genomic localization of individual 5mC residues is bisulfite sequencing (Frommer et al. (1992) *Proc Natl Acad Sci USA* 89, 1827-1831) and its numerous modifications. This method is based on bisulfite-mediated deamination of C to U; 5mC residues are inert to this reaction, and therefore standard sequencing of bisulfite-converted DNA shows 5mC residues in the C-track, whereas T and C residues—in the T-track. If treated with bisulfite, hmC is converted to cytosine 5-methylsulfonate, which is deaminated at an even slower rate than 5mC (Hayatsu, M. & Shiragami, M. (1979) *Biochemistry* 18, 632), and should thus appear in the C-track. Therefore, hmC residues cannot be distinguished from mC residues using conventional bisulfite sequencing protocols. Similarly, other high-throughput genome-wide analysis techniques such as mDiP (methylated DNA immunoprecipitation) (Weber et al. (2005) *Hum Mol Genet.* 14, R11-R18), which is based on binding m5C-containing DNA fragments to 5mC-specific antibodies, or methods based on using methylation sensitive restriction endonucleases, are not suitable for detection of hmC residues either. Therefore, as all the existing techniques were designed to distinguish only the two alternate states of cytosine (methylated versus unmodified) (Schumacher et al. (2006) *Nucleic Acids Res.* 34, 528-542), they have none or poor ability to determine hmC residues in genomic DNA.

Recently, a method for DNA derivatization using non-cofactor reactions of DNA methyltransferases has been disclosed (patent application LT2009023 filed Feb. 4, 2009). This technique permits methyltransferase-directed sequence-specific covalent coupling of formaldehyde (or other aliphatic aldehydes) to the C5-position of their target cytosine residues in DNA, thereby producing 5-hydroxymethylated (or 5-hydroxyalkylated-) cytosines. The application also describes methods for subsequent sequence-specific covalent derivatization of hmC residues in various types of DNA molecules by methyltransferase-directed coupling of nucleophilic compounds, including thiols. The latter reaction in principle permits derivatization of hmC residues in DNA with various functional and reporter groups provided that they occur at a target position for the directing MTase. Since hmC residues are known to occur at CG sequences in genomic DNA of vertebrate animals including humans, some of the derivatization reactions may be useful in developing the required techniques for analysis of hmC in DNA. However, these derivatization reactions have not been assessed with respect to their suitability for chemical manipulation and analysis of hmC residues in various types of DNAs, including mammalian genomic DNA.

In conclusion, it is obvious that new reliable and validated methods are required for analysis of hmC resides in genomic DNA.

SUMMARY OF THE INVENTION

This problem can be overcome by providing the embodiments of the present invention.

The key idea of the present invention relates to the targeted conversion of hydroxyalkylated residues in a biomolecule in the presence of a directing methyltransferase. Such hydroxyalkylated residues in a biomolecule, that are the target residues of a directing methyltransferase, were found by the authors to be selectively converted to unmodified residues or to derivatized residues in the presence of the methyltransferase. One example of substrate-activating methyltransferases is pyrimidine-5 specific methyltransferases, which naturally catalyze the transfer of a methyl group to the 5 position of cytosine or uracil residues in DNA, RNA or free nucleotides by making a transient covalent bond to the 6 position of the pyrimidine ring.

The present invention covers a use of a cofactor-free methyltransferase for targeted conversion of a modified biomolecule, bearing a modifying moiety of formula —CH(OH)—R, wherein R is hydrogen or $C_1$-$C_{12}$-alkyl, preferably hydrogen or lower alkyl, into an unmodified biomolecule by removal of said modifying moiety at the methyltransferase target site.

The present invention also covers a method for targeted conversion of a modified biomolecule, comprising incubation of the modified biomolecule, bearing a modifying moiety of formula —CH(OH)—R, wherein R is hydrogen or $C_1$-$C_{12}$-alkyl, preferably hydrogen or lower alkyl, with a cofactor-free directing methyltransferase under conditions compatible with enzymatic activity of the methyltransferase, wherein said targeted conversion results from: i) covalent removal of said modifying moiety at the target site; or ii) derivatization of said modifying moiety at the target site by covalent coupling of non-cofactor nucleophilic compound(s) of general formula HQ-LX, wherein X represents a functional group or a reporter group attached via a linker L, and Q is selected from S, Se, O, N, C.

In the preferred embodiments of present invention R is hydrogen or —$CH_3$ and Q is S or Se. The biomolecule is a nucleic acid molecule, preferably DNA. Said methyltransferase is a DNA cytosine-5 methyltransferase, selected from the group consisting of M.HhaI, M.SssI, and M.HpaII or derivatives thereof.

The modified biomolecule used in the present invention is a naturally or artificially modified biomolecule, bearing a modifying moiety mentioned above at the target residue.

The method according to present invention also applies to a method for targeted labeling of a modified biomolecule, comprising a direct or subsequent incorporation of a reporter group, which is suitable as a label and which allows for the identification of the labeled molecule among other unlabeled molecules.

The present invention also relates to a method for detecting hydroxymethylated target sites in a biomolecule, comprising derivatization or labeling of the biomolecule by coupling non-cofactor nucleophilic compounds of present invention in the presence of a cofactor-free methyltransferase and detecting whether the target sites of said methyltransferase have been modified, wherein modification of the target site of said methyltransferase is indicative of the presence of hydroxymethylated target site. The method of present invention extends to the cases, wherein the coupled compound(s) is added to a 5-hydroxymethylcytosine residue in DNA and cannot be added to a 5-methylcytosine or a cytosine residue.

Finally, the present invention relates to a kit comprising a cofactor-free directing methyltransferase or a cofactor-free directing methyltransferase and an non-cofactor nucleophilic compound(s), suitable buffer components and further comprising aldehyde scavenging compounds for performing any of the methods above.

DESCRIPTION OF DRAWINGS

To illustrate the main characteristic features of the present invention this description contains:

20 nM hmC-containing cognate oligodeoxynucleotide duplex was treated with catalytically active or C81S mutant M.HhaI (lanes 2, 3), with catalytically active or thermally inactivated M.HpaII (lanes 5, 6) or catalytically active or thermally inactivated M.SssI (lanes 8, 9) for 1 hour at room temperature.

FIG. 7: Gel electrophoretic analysis of methyltransferase-directed modification of a 618 bp 5-hydroxylalkylcytosine-containing DNA fragment. The DNA fragment (100 nM) containing hmC residues at the target CG sites was incubated with 1,4-dithiothreitol in the presence of M.HhaI or M.SssI and then treated with a Oregon Green maleimide. Labeled DNA was analyzed by 2% agarose gel electrophoresis. Imaging of the fluorescein reporter was performed using a 473 nm laser scanner (left panel), DNA fragments were visualized after staining with ethidium bromide (right panel). Lane 2, M.SssI; lane 3, M.HhaI; lane 1, control with MTase omitted.

DETAILED DESCRIPTION OF THE INVENTION

The major scope of the present invention is the use of a methyltransferase for targeted conversion of alpha-hydroxyalkylated residues in a biomolecule by covalent detachment or extension of the alpha-hydroxyalkyl side chain in a target residue of the biomolecule.

The general principle of targeted conversion of alpha-hydroxyalkylated residues in a biomolecule according to the present invention can be understood from the Scheme 1 below which shows possibilities of conversion of 5-alpha-hydroxyalkylcytosine residues in DNA in the presence of DNA cytosine-5 methyltransferases (MTase).

Scheme 1. Sequence specific conversion of alpha-hydroxyalkylated residues in DNA with DNA methyltransferases according to the present invention. Reaction 1: targeted removal of alpha-hydroxyalkyl groups from target cytosine residues in DNA; Reaction 2: targeted derivatization of alpha-hydroxyalkyl groups in target cytosine residues in DNA.

R = ——H, ——CH$_3$
QH = SH, SeH, NH$_2$
LX = ——CH$_2$CH(CO$_2$H)NH$_2$
——CH$_2$CH(OH)CH(OH)CH$_2$SH
——CH$_2$CH$_2$OH
-5'-adenosyl
——CH$_2$CH$_2$NH$_2$
——CH$_2$CH(OH)CH(OH)CH$_2$SH
——OH In support of the novelty and inventive step of the present invention it should be noted:

1) the reaction of removal of alpha-hydroxyalkyl groups from cytosine residues described in the present invention (Reaction 1 in Scheme 1) is novel and is not obvious to the skilled person. The described reaction is atypical for MTases, which naturally catalyze cofactor-dependent targeted transmethylation (nucleophilic substitution $S_N2$), including reactions with AdoMet analogs.

2) targeted removal 5-alpha-hydroxyalkyl groups including 5-hydroxymethyl groups from cytosine residues DNA (Reaction 1 in Scheme 1) cannot be achieved by any means described in the prior art.

3) derivatization of 5-alpha-hydroxyalkyl cytosine residues (including hmC) in DNA by targeted coupling of nucleophilic compounds (Reaction 2 in Scheme 1) has been described previously as a second step of a two-step procedure for sequence-specific derivatization of unmodified DNA (LT2009023). In the present invention it is shown that naturally occurring hmC residues in DNA can also be derivatized and then labeled in a similar manner.

In a preferred embodiment of the present invention, R comprises H and —$CH_3$, and -QH comprises —SH and —SeH. However it is obvious to the person skilled in the art that R might be easily extended to $C_1$-$C_{12}$ alkyl, alkenyl, alkynyl, and -QH to cover at least —OH, —$NH_2$, —$NHNH_2$ or —$ONH_2$, $N_3H$, NCH (or corresponding salts in which a hydrogen atom is replaced by a cation, such as a metal ion or an ammonium ion) as well as other suitable nucleophiles that are sufficiently active in aqueous buffers in the pH range of 4-10. In preferred embodiments of the present invention, L is —$CH_2CH(CO_2H)$—, but it is understandable to the skilled person that L is also covering another suitable linker groups ranging from just a mere covalent bond to a combination of linear, cyclic and/or aromatic moieties optionally connected with —NHCO—, —O—, —S— connectors, (poly)ethyleneglycol chains —$(CH_2CH_2O)_n$— n=1-100, etc.

Treatment of 5-hydroxyalkylcytosine-containing DNA with an exogenous nucleophilic compound HQ-LX (wherein LX comprises a chemical reactive group or a reporter group X attached via a linker L) in the presence of a directing DNA cytosine-5 methyltransferase permits sequence-specific coupling of the compound to give incorporation of the LX group via a thiomethyl anchor (when QH=—SH) at the target cytosine residues. The chemical reactive group X can then be used for covalent ligation with a suitable compound carrying a reporter group (see below).

When QH=SeH, a similar work out leads to targeted incorporation of the LX group via a selenomethyl anchor into DNA, as demonstrated in Examples 2 and 5. The chemical reactive group X can then be used for covalent ligation with a suitable compound carrying a reporter group. Selenides, which are part of the selenomethyl anchor, can be readily oxidized to selenoxides by treatment with $H_2O_2$ or $NaIO_4$. Since selenoxides can subsequently undergo elimination with the cleavage of a Se—C bond (Wirth, T. (2000) *Angew. Chem. Int. Ed.* 39, 3740-3749; Gieselman et al. (2002) *ChemBioChem* 3, 709-716), the selenomethyl anchor can thus be used as a chemically cleavable covalent linker in affinity purifications of labeled biomolecules. On the other hand, the presence of a Se atom in the attached group can be used for applications such as crystallographic determination of biomolecular structure via multi-wavelength anomalous dispersion (MAD) technique due to significant anomalous scattering of X-rays. The presence of the $^{77}Se$ nucleus (natural abundance of 8%) with a S=½ magnetic spin may also find applications in NMR and EPR spectroscopy (Zelakiewicz et al. *J. Am. Chem. Soc.*, 2004, 126, 8112-8113).

Further development of the proposed method for targeted conversion of hmC residues in DNA is a method for targeted labeling a biomolecule comprising modification (derivatization) of the biomolecule according to LT2009023 and, accompanied by incorporation of a group that is suitable as a label and that allows for the identification of the labeled biomolecules among other unlabeled molecules.

In a preferred embodiment of the present invention sequence-specific labeling of DNA was achieved by DNA methyltransferase-directed coupling of L-cysteine (thiol) followed by chemo-selective ligation with an e.g. affinity label, such as amine-reactive biotin.

Scheme 2. Selective sequence-specific covalent labeling of hmC residues in DNA using DNA methyltransferases according to the present invention. The attached reporter moiety is shown as a ball.

Labeled DNA

Scheme 2 above demonstrates the principle of such sequence-specific labeling of hmC-containing genomic DNA achieved by (1) treatment of hmC-containing DNA with L-cysteine in the presence of the HhaI methyltransferase, followed by (2) amino-selective ligation of a reporter moiety with an N-hydroxy-succinimide ester.

In the preferred embodiment of the present invention, (a) the noncofactor nucleophilic compound or a subsequent derivative thereof contains a fluorescent label; and (b) hydroxymethylated targets sites are detected by the presence of fluorescence in said nucleic acid molecule.

In a preferred embodiment of the present invention sequence-specific fluorescent labeling of DNA was achieved by DNA methyltransferase-directed coupling of 1,4-dithiothreitol followed by chemo-selective ligation with an e.g. affinity label, such as thiol-reactive fluorophore (Example 13).

In another preferred embodiment of the present invention, the label of said detectable compound is detected by (a) an antibody specifically binding to the label of said detectable compound or by (b) avidin or streptavidin specifically binding to the label of said detectable compound.

As mentioned, numerous ways to achieve targeted labeling or targeted derivatization of biopolymers can be realized according to present invention. For this purpose a noncofactor nucleophilic compound should typically contain a chemical moiety LX, wherein X comprises a functional group or a reporter group that is attached via a linker group L.

Many chemo-selective ligations defining the reactive groups X are available for attaching a label to the modified biomolecule in aqueous solution. Classical ligations (Garman, (1997) Non-radioactive labeling: A practical introduction, Academic Press) involve primary amino groups which can be reacted with amine reactive groups like N-hydroxy-succinimidyl ester, acyl azide, acyl nitrile, acyl chloride, pentafluorophenyl ester, thioester, sulfonyl chloride, isothiocyanate, imidoester, aldehyde or ketone leading to stable amides, sulfonamides, thioureas, imidates or imines, which can be reduced to stable secondary amines. Thiols specifically react with haloacetamides, maleimides, aziridines or other thiols leading to thioether or disulfide linkages and 1,2-diols can be modified with arylboronic acids. Hydrazines or hydroxylamines can be condensed with aldehydes or ketones leading to hydrazones or oximes. 1,2-Aminothiols selectively react with aldehydes or thioesters to form thiazolidines (e.g. N-terminal cysteine residues of polypeptides, Liu and Tam, (1994) *Proc. Natl. Acad. Sci. USA* 91, 6584-6588) or stable amide bonds (e.g. N-terminal cysteine residues of polypeptides, native chemical peptide ligation, Dawson et al., (1994) *Science* 266, 776-779); azides can be reacted with alkynes (Huisgen 1,3-dipolar cycloaddition, Lewis et al. (2002), *Angew. Chem. Int. Ed.* 41, 1053-1057) or with phosphane esters (Staudinger ligation, Saxon and Bertozzi, (2000) *Science* 287, 2007-2010) to form 1,2,3-triazoles or amides; Diels-Alder cycloadditions between activated dienes and dienophiles (e.g. furanes and maleimides, Graham et al., (2002) *Tet. Lett.* 4785-4788) are feasible in aqueous solution. Other modern palladium-catalyzed cross-coupling reactions between arylhalides and terminal alkynes (Sonogashira coupling, Casalnuova and Calabrese, (1990) *J. Am. Chem. Soc.* 112, 4324-4330; Dibowski and Schmidtchen, (1998) *Angew. Chem. Int. Ed.* 37, 476-478; Bong and Ghaderi, (2001) *Org. Lett.* 3, 2509-2511) or between arylhalides and arylboronic acids (Suzuki coupling, Casalnuova and Calabrese, (1990) *J. Am. Chem. Soc.* 112, 4324-4330; DeVasher et al., (2004) *J. Org. Chem.* 69, 7919-7927) yielding arylalkynes or biaryls could be used. Additionally, copper-catalyzed alkyne coupling reactions between terminal haloalkynes and terminal alkynes or terminal silylalkyne leading to conjugated diynes can be performed in aqueous solution. Finally, fluorogenic derivatization reagents like 4-halo-7-nitrobenzofurazan, N-methylisatoic anhydride or activated bimanes can be used to label transferred thiol, amino or hydroxyl groups directly.

Nucleic acids generally do not contain highly nucleophilic or electrophilic centers. Thus, besides the cycloadditions, palladium-catalyzed cross-coupling reactions or copper-catalyzed alkyne coupling reactions, many other reactions between nucleophiles and electrophiles with interchangeable reactive group X could be used for sequence-specific labeling of nucleic acids.

In the preferred embodiment of the present invention X comprises at least one functional group, selected from a primary amino group, a thiol group, a 1,2-diol group, a haloacetamide group, a maleimide group, an aldehyde group, a ketone group, an azido group, an alkyne group, a 1,3-diene function, a dienophilic function, an arylhalide group, a terminal alkyne group, an arylboronic acid group, a terminal haloalkyne group, a terminal silylalkyne group and a protected amino, thiol, 1,2-diol, hydrazino, hydroxyamino, aldehyde, ketone and 1,2-aminothiol group. For the purposes of labeling of biopolymers X also comprises heavy atoms or heavy atom clusters suitable for phasing of X-ray diffraction data, radioactive or stable rare isotopes, and a residue of a member selected from fluorophores, fluorescence quenchers, chromophores, affinity tags, spin labels (stable paramagnetic groups), groups containing radioactive or stable rare isotopes, groups containing heavy atoms suitable for phasing X-ray diffraction data, crosslinking agents, nucleic acids cleaving groups, haptens, nanoparticles and beads.

Two major strategies could be used to identify hmC residues in genomic DNA (Scheme 3).

A. One strategy is based on selective conversion of hmC residues to unmodified cytosine residues. This approach is can be used with existing analysis methods that normally can reveal positions of 5mC and unmodified C in DNA, but do not distinguish hmC from 5mC. For example, bisulfite sequencing will show the positions of 5mC+hmC residues in the C-track and positions of unmodified cytosines in the T-track. Selective Mtase-directed conversion of hmC to C and subsequent bisulfite sequencing the converted DNA would then reveal positions of 5mC residues in the C-track, and positions of hmC+C residues in the T-track. Comparison of the two datasets will display hmC residues as bands that migrated from the C-track to the T-track upon enzymatic conversion.

B. Another strategy is based on selective derivatization of hmC residues such that they can be directly distinguished from 5mC and C residues. For example, selective coupling of thiols or selenols in the presence of directing DNA Mtases will lead to corresponding thiomethyl or selenomethyl derivatives. Such derivatives can be used to attach reporter or affinity groups (see Scheme 2).

Scheme 3. Sequence specific conversions of natural DNA with DNA methyltransferases according to the present invention for analytical determination of hmC residues. A. conversion of hmC residues to unmodified cytosines; B. derivatization/labeling of hmC residues.

Cytosine (C) and its C-5 modification products in DNA
(hmC and 5mC)

In yet another preferred embodiment of the present invention, (a) the attached moiety interferes with nucleic acid amplification at the recognition sites of the methyltransferase; and (b) hydroxymethylated target sites are detected by testing whether amplification of the nucleic acid molecule at the recognition sites of the methyltransferase has been retarded. Retardation of amplification may be achieved by interfering with primer binding or with strand elongation during an amplification reaction.

During the methods of present invention, a step of nucleic acid sequencing may be performed. Any methods known in the art may be used for sequencing.

In a preferred embodiment of the present invention, PCR is real-time PCR. In another preferred embodiment of the present invention, nucleic acid amplification is carried out by real-time PCR.

In another preferred embodiment of the present invention, (a) nucleic acid molecules modified at the methyltransferase recognition sequence are purified by affinity purification; and (b) the compounds of formulas (I) used in the present invention or a derivative thereof contains an affinity tag.

In preferred embodiments, the methods of the present invention comprise after the step of targeted modification of a biomolecule an additional step of sequencing the DNA molecule. Any methods known in the art may be used for sequencing.

Examples provided in the present invention (Example 3, FIG. 3) show that an exogenous nucleophilic compound or a derivative thereof is added to a 5-hydroxymethylcytosine residue and cannot be added to a 5-methylcytosine residue or cytosine residues in DNA.

In yet another preferred embodiment of the present invention, the identity of said DNA molecule is determined by DNA sequencing, hybridization, MALDI-TOF or analysis of nucleoside composition by enzymatic fragmentation and chromatography.

Finally, in one of the preferred embodiments, the kit of the present invention comprises a methyltransferase or methytransferase and a non-cofactor nucleophilic compound in separate containers and may further contain an information leaflet or instruction for use.

Scavenging compounds can be a further component of such a kit, supplied to sequester the aldehyde released from the reaction such that to preclude it from entering the reverse reaction. All classes of water soluble compounds that react with aldehydes (thiols, primary amines, hydroxylamines, hydrazines) can be used. These compounds can also be supplied in a chemically altered form such as modified with a protecting group, containing a sterically demanding group (to prevent their reactivity as active nucleophiles with respect to the biomolecule), in an oligomeric or polymeric form that releases the compound(s) when brought into a suitable milieu such as a methyltransferase buffer, or immobilized to a polymer or a bead. For example thiols exist in an oxidized form as disulfides or polysulfides etc., which easily convert to thiols under reducing conditions. Auxiliary biomolecules containing the above functional groups (for example proteins such as bovine albumin, etc) can also be as scavenging agents provided that they contain no target residues for the directing MTase.

In another preferred embodiment the present invention also relates to a kit containing a methyltransferase and/or diagnostic formulation(s) on the basis of above. In one of the embodiments of present invention the diagnostic formulation is a liquid composition. The preferred solvent of the diagnostic formulation is aqueous in nature. In addition, the formulation may contain other ingredients or carriers for modifying or maintaining the pH, osmolarity, viscosity, clarity, color, sterility, stability, rate of dissolution, or odor of the formulation. Similarly, the formulation may contain still other pharmacologically acceptable ingredients for modifying or maintaining the stability, rate of dissolution, release, or absorption of the diagnostic composition. Once the diagnostic formulation has been formulated, it may be stored in sterile vials as a solution, suspension, gel, emulsion, solid, or dehydrated or lyophilized powder. Such formulations may be stored either in ready to use form or requiring reconstitution immediately prior to use.

In practice for the preparation of an unmodified biomolecule according to the present invention the following steps are to be carried out:

a) combining (putting together) the modified biomolecule and a cofactor-free MTase in a suitable aqueous buffer that is compatible with enzymatic activity of the methyltransferase (for example: 50 mM MOPS, 50 mM MES pH 7.5, 1 mM Na$_2$EDTA, 15 mM NaCl, 0.2 mg/ml bovine serum albumin, 5% glycerol; or 10 mM Tris-HCl pH 7.4, 50 mM NaCl, 0.5 mM Na$_2$EDTA 0.2 mg/ml bovine serum albumin, 5% glycerol; or other similar buffer recommended by a MTase manufacturer);
b) incubation of the reaction at a temperature that is compatible with enzymatic activity of the methyltransferase (as recommended by a MTase manufacturer) for a period of 5-120 min;
c) stopping the reaction (by adding an inhibiting compound, diluting the reaction with a suitable solvent, flash-freezing at −20° C. or lower temperature, or inactivating the methyltransferase by heating at 40° C. above the optimal reaction temperature for 5-20 min);
d) isolation of the unmodified biomolecule as necessary.

For the preparation of a derivatized biomolecule according to the present invention the following steps are to be carried out:
a) combining (putting together) the biomolecule, a cofactor-free MTase and a non-cofactor nucleophilic compound in a suitable aqueous buffer (see above);
b) incubation of the reaction at a temperature that is compatible with enzymatic activity of the methyltransferase for a period of 5-120 min;
c) stopping the reaction (see above);
d) isolation of the unmodified biomolecule as necessary.

Normally, directing MTases are supplied at near equimolar amounts with respect to biomolecular target sites. A non-cofactor nucleophilic compound is typically supplied at a millimolar concentration.

EMBODIMENTS OF THE INVENTION

Represented below are specific examples of the embodiments of the present invention. The scope of the invention is only illustrated by these examples without being restricted to them.

Examples 1-2

Sequence-specific modifications of hmC-Containing oligodeoxyribonucleotide duplexes with the HhaI DNA cytosine-C5 methyltransferase.

Modification was first performed in the presence of the HhaI DNA cytosine-05 methyltransferase (M.HhaI) using short duplex oligodeoxyribonucleotides. M.HhaI recognizes the 5'-GCGC-3' target site in DNA and naturally transfers the methyl group of S-adenosyl-L-methionine (SAM or AdoMet) to the C5 position of the inner cytosine residue (underlined). Following the enzymatic modification reactions, a duplex oligodeoxynucleotide was enzymatically fragmented to 2'-deoxynucleosides and analyzed by reversed-phase HPLC coupled with ESI-MS.

The duplex oligodeoxynucleotide I:II was produced by annealing single-stranded oligonucleotide I (SEQ ID NO:1) (5'-TAATAATGCGCTAATAATAATAAT) and II (SEQ ID NO:2) (3'-TTATTACGCGATTATTATTATTA) in water as described in LT2009023. hmC modification was introduced enzymatically as described in LT2009023. Modification removal reactions were performed by incubating the hmC-modified duplex oligonucleotide I:II (13 μM) with M.HhaI (15 μM) for 2 hour at 37° C. Derivatization reactions were performed by incubating the modified duplex oligonucleotide I:II (13 μM) with 1 mM L-selenocysteine in the presence of M.HhaI (15 μM) for 1 hour at 20° C. For nucleoside composition analysis DNA was isolated as described in LT2009023 and treated with Nuclease P1 (2 u, Sigma, Germany) for 2 hours at 60° C. and calf intestine alkaline phosphatase (30 u, Fermentas Life Sciences, Lithuania) overnight at 37° C. Obtained nucleosides were analyzed by reverse-phase HPLC (Discovery C18 75×2.1 mm, 3 μm column, equipped with a Supelguard Discovery C18 20×2.1 mm, 5 μm precolumn, Supelco, Germany) coupled with a mass spectrometric detector (HP 1100 series ESI-MS equipped with singe quadruple). Compounds were eluted with a linear gradient of solvents A (20 mM ammonium acetate pH 5.5) and B (80% aqueous methanol) at a flow of 0.3 ml/min at 30° C. as follows: 0-20 min, 0-20% B; 20-22 min, 20-100% B; 22-27 min, 100% B. Analytes were detected by an in-line diode array UV absorbance detector. UV absorbance spectra were acquired (190-400 nm wavelength interval) at peak maxima and solvent contributions were removed by subtracting background spectra before and after the peaks. For online mass spectrometric detection post-column mobile phase modification (equal co-flow of 96% methanol, 4% formic acid and 1 mM sodium hydroxide) was used to enhance the detection efficiency of 2'-deoxycytidine and its derivatives. Mass spectra were recorded in 50-600 m/z range in the positive ion mode. Ionization capillary voltage was 5000 V, fragmenter voltage was 100-120 V, drying gas temperature was 300-350° C. and flow rate was 10-12 L/min. High-resolution mass spectra (HR-MS) were acquired by analysis of corresponding HPLC fractions on a LTQ Orbitrap mass spectrometer (Thermo Electron) equipped with a Proxeon NanoSpray ESI.

Example 1

Nucleoside composition analysis of a hmC-containing duplex oligodeoxyribonucleotide after treatment with M.HhaI.

Figure 1:
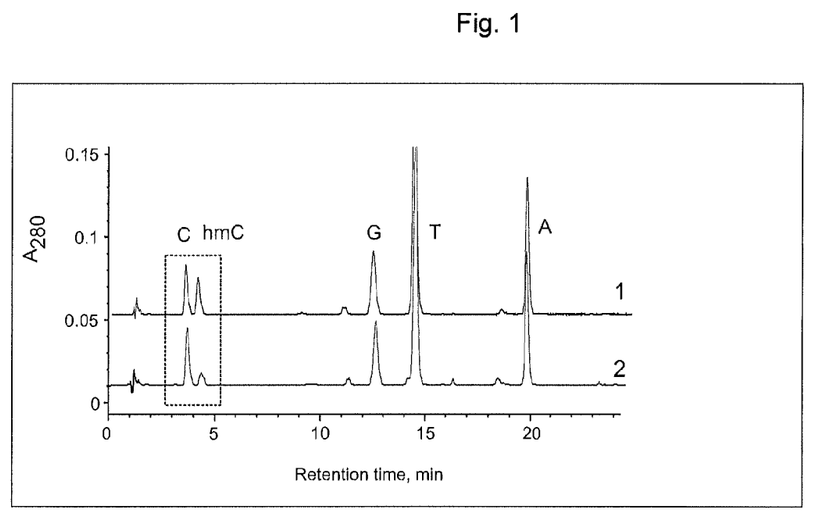
FIG. 1: Reversed-phase HPLC analysis of enzymatically fragmented duplex oligodeoxynucleotides obtained after treatment with M.HhaI. hmC-containing DNA duplex I:II (13 μM) was treated with M.HhaI (15 μM) for 2 hours at 37° C. (trace 2). Control reaction (trace 1) lacked M.HhaI. Boxed area contains peaks corresponding to dC and hmdC.

HPLC analysis of nucleoside composition of the modified duplex oligodeoxyribonucleotide (I:II) revealed, besides dG, dT and dA nucleosides, the presence of dC and dC$^{CH_2OH}$ (hmC 2'-deoxynucleoside) with a retention times of 3.7 and 4.2 min, respectively (see FIG. 1). These compounds were analyzed by coupled ESI-MS (m/z: 250 [M+Na]$^+$, 134 [cytosine+Na]$^+$ and m/z: 280 [M+Na]$^+$, 164 [5-hydroxymethylcytosine+Na]$^+$). The observed masses are in agreement with 2'-deoxycytidine dC and 5-hydroxymethyl-2'-deoxycytidine dC$^{CH_2OH}$, respectively. The latter compound was nearly fully converted to unmodified dC upon incubation with M.HhaI (compare the relative size of C and hmC peaks in traces 1 and 2). Thus the hydroxymethyl group is removed from the 5-hydroxymethylcytosine residue in DNA by M.HhaI.

Examples 2-6

Sequence-specific modifications of internally labeled hmC-containing oligodeoxyribonucleotide duplexes with a DNA cytosine-05 methyltransferase DNA modification was investigated in the presence of a directing DNA cytosine-5 MTase M.HhaI, M.SssI, or M.HpaII. M.HhaI recognizes the double-stranded DNA sequence 5'-GCGC-3' and naturally transfers the methyl group of S-adenosyl-L-methionine (SAM or AdoMet) to the C5 position of the inner cytosine residue (underlined). Accordingly, other DNA methyltransferases perform a similar reaction but they recognize different DNA target sequences: M.SssI (recognition target CG), or M.HpaII (recognition target CCGG). Analysis of modifications of a target cytosine residue in the presence of a DNA cytosine-C5 methyltransferase was performed using internally labeled duplex oligodeoxyribonucleotides. Internally labeled duplex oligodeoxyribonucleotides contained a cognate target sequence of a DNA methyltransferase in which a target cytosine residue (or a target residue and another cytosine residue for M.HhaI) were $^{33}$P-labeled. hmC modification was introduced enzymatically by incubation of the duplex oligodeoxynucleotide with formaldehyde (13 mM) and a corresponding MTase.

For composition analysis, a duplex oligodeoxynucleotide was enzymatically fragmented to 2'-deoxynucleoside-5'-monophosphates and then analyzed by TLC and autoradiography permitting selective observation of modifications of the target nucleotide.

The duplex oligodeoxyribonucleotides III:IV (unmethylated duplex for M.HhaI), V:VI (hemimethylated duplex for M.HhaI), VII:VIII (duplex for M.HpaII and M.SssI) were produced by mixing equal molar amounts (150 μM) of complementary single-stranded oligodeoxyribonucleotide III (SEQ ID NO:3) (5'-TCGGATGTTGTGGGTCA) and IV (SEQ ID NO:4) (3'-GCCTACAACACCCAGTCGCGTAC-TATCACAT); V (5'-TCGGATGTTGTGGGTCAG) (SEQ ID NO:5) and VI (SEQ ID NO:6) (3'-GCCTACAACAC-CCAGTCGMGTACTATCACAT); VII (SEQ ID NO:7) (5'-TGACCCACGCTCGCC) and VIII (SEQ ID NO:8) (3'-ACTGGGTGCGAGCGGGCCTCTATTTAATACA) in water, heating at 95° C. for 5 min and slow cooling to room temperature. Labeled duplexes were prepared by mixing DNA duplex (400 nM), dATP, dGTP and dTTP (33 μM of each), [α-33P]CTP (1.5 μM, Hartmann Analytic, Germany) and Klenow Fragment (0.16 u/μL, Fermentas Life Sciences) and incubating in Klenow reaction buffer at 37° C. for 30 min following incubation at 75° C. for 15 min. 20-100 nM DNA duplexes were then treated with 125 nM M.HhaI, 1000 nM M.HpaII, or 120 nM M.SssI in buffer (5-20 μL, 50 mM MOPS, 50 mM MES pH 7.0 (for M.HhaI) and pH 7.5 (for other methyltransferases), 1 mM Na$_2$EDTA, 15 mM NaCl, 0.2 mg/ml bovine serum albumin, 5% glycerol) and 13 mM formaldehyde for 1 hour. Modification removal reactions were performed by incubating a 20 μM duplex oligodeoxyribonucleotides with a cognate DNA methyltransferase (2 μM M.HhaI, 2 μM M.HpaII or 1.2 μM M.SssI) for 2-5 hours at 37° C. in buffer (10 mM Tris-HCl pH 7.4, 50 mM NaCl, 0.5 mM Na$_2$EDTA 0.2 mg/ml bovine serum albumin, 5% glycerol). For labeled nucleotide analysis, DNA was precipitated with 3 volume of ethanol, dissolved in nuclease BAL31 buffer (5 μL) with nuclease BAL31 (0.4 u) (Fermentas Life Sciences) and incubated for 1 hours at 30° C. 0.5-3 μl aliquotes were spotted on TLC plates (PEI CelluloseF, 20×20 cm, Merck). TLC plates were eluted with isobutyric acid/water/conc. ammonia, (66:17:4, vol/vol/vol). Plates were dried overnight and radioactive bands were autoradiographed to an imaging plate (Fujifilm, Japan) followed by scanning with a FLA-5100 phosphoimager. Radioactive spots were quantitated using MultiGauge software (Fujifilm). Modified 2'-deoxy-5'-mononucleotides (dXMP) were detected as radioactive spots in addition to the major spot of 2'-deoxycytosine-5'-monophosphate (dCMP). The position of a modified nucleotide (X) relative to that of the unmodified C nucleotide (dCMP) (Rc (X)=R$_f$(dXMP)/R$_f$(dCMP)) was determined and was used for its chromatographic identification.

Example 2

Target nucleotide analysis in a hmC-containing duplex oligodeoxyribonucleotide after treatment with the HhaI DNA cytosine-5 methyltransferase (M.HhaI).

Figure 2:
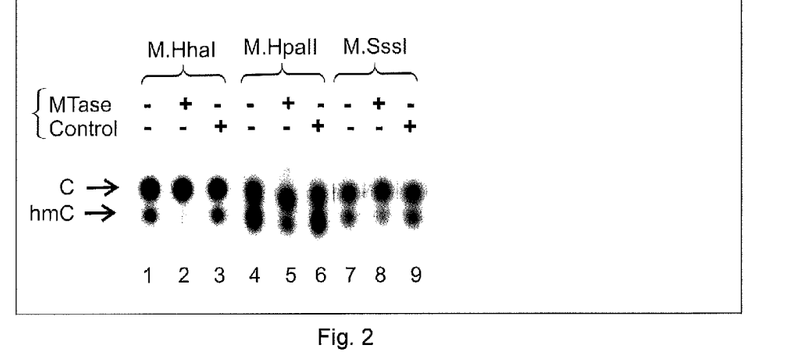
FIG. 2: TLC analysis of [$^{33}$P]-labeled 2'-deoxy-5'-mononucleotides of enzymatically fragmented duplex oligodeoxynucleotides after treatment with M.HhaI, M.HpaII and M.SssI.

TLC analysis of modification products obtained after treatment of hmC-containing DNA duplex with M.HhaI indicated a decrease of the ratio of hmC and C nucleotides (Rc values of 0.85 and 1.0) (see FIG. 2, lanes 1 and 2). Control reaction (lane 3) contained catalytically inactive mutant (C81S) of M.HhaI. Thus the 5-hydroxymethyl group is removed from the target hmC residue yielding unmodified cytosine in the presence of catalytically active M.HhaI.

Example 3

Target nucleotide analysis in duplex oligodeoxyribonucleotides containing hmC, C or 5mC at the target position after treatment with L-cysteine and the HhaI DNA cytosine-5 methyltransferase (M.HhaI).

20 nM duplex oligodeoxyribonucleotides V:VI (cognate-C), V:VI-methylated (cognate-5mC), V:VI-hydroxymethylated (cognate-hmC), VII:VIII (nonspecific-C) or VII:VIII-hydroxymethylated (nonspecific-hmC) (FIG. 3, lanes 1-5, respectively) was incubated with 50 mM L-cysteine and M.HhaI (120 nM) for 1 hour at room temperature. An additional labeled spot (R$_C$=0.55) corresponding to coupling product Cys-hmC was observed (lane 3) only when the cognate-hydroxymethylated DNA was used as a substrate. Thus M.HhaI adds exogenous nucleophiles in a sequence-specific manner to hmC residues, but not to C or 5mC residues.

Example 4

Target nucleotide analysis in a hmC-containing duplex oligodeoxyribonucleotide after treatment with L-selenocysteine and the DNA cytosine-5 methyltransferase (M.HhaI).

Figure 3:
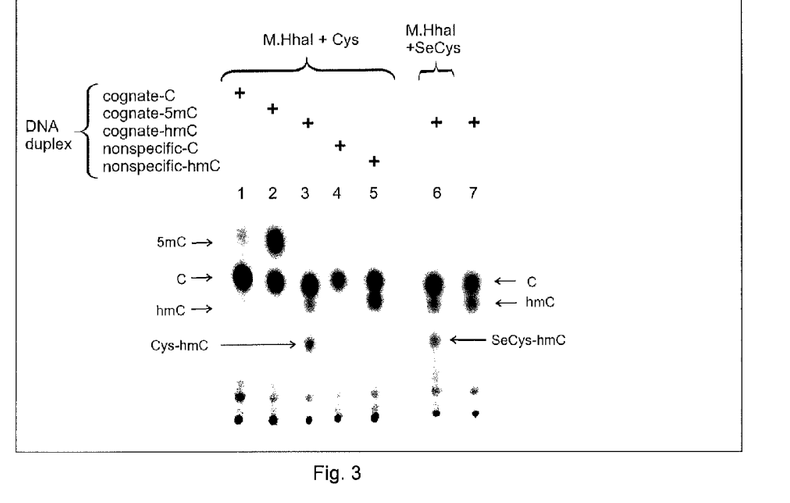
FIG. 3: TLC analysis of [$^{33}$P]-labeled 2'-deoxy-5'-mononucleotides of enzymatically fragmented duplex oligodeoxynucleotides after treatment with cysteine or selenocysteine in the presence of M.HhaI. 20 nM oligodeoxynucleotide duplexes containing C, 5mC, hmC at the target residues position of the GCGC site or an C or hmC residue in the CCGG site as shown all were treated with M.HhaI (lanes 1-6), and 50 mM L-cysteine (lanes 1-5) or 1 mM L-selenocysteine (lane 6) for 1 hour at room temperature.

TLC analysis of modification products obtained after treatment of hmC-containing cognate DNA duplex with L-selenocysteine and M.HhaI indicated the appearance of a new modified nucleotide SeCys-hmC (Rc value of 0.6; FIG. 3, compare lanes 6 and 7). Thus L-selenocysteine is coupled to the target 5-hydroxymethylcytosine residue in DNA in the presence of M.HhaI.

Example 5

Target nucleotide analysis in a hmC-containing duplex oligodeoxyribonucleotide after treatment with the SssI DNA cytosine-5 methyltransferase (M.SssI).

TLC analysis of modification products obtained after treatment of hmC-containing DNA duplex with M.SssI indicated a decrease of the ratio of hmC and C nucleotides (FIG. 2, compare lanes 7-8). Control reaction (lane 9) contained thermally inactivated M.SssI. Thus the 5-hydroxymethyl group is removed from the target hmC residue yielding unmodified cytosine in the presence of catalytically active M.SssI.

Example 6

Target nucleotide analysis in a hmC-containing duplex oligodeoxyribonucleotide after treatment with the HpaII DNA cytosine-5 methyltransferase (M.HpaII).

TLC analysis of modification products obtained after treatment of a hmC-containing DNA duplex with M.HpaII indicated a decrease of the ratio of hmC and C nucleotides (FIG. 2, compare lanes 4-5). Control reaction (lane 6) contained thermally inactivated M.HpaII. Thus the 5-hydroxymethyl group is removed from the target hmC residue yielding unmodified cytosine residue in the presence of catalytically active M.HpaII.

Examples 7-11

Sequence-specific modifications of large DNA molecules containing 5-hydroxyalkyled target cytosine residues with a DNA cytosine-C5 methyltransferase.

Sequence-specific modifications by DNA cytosine-05 methyltransferases HhaI, SssI and HpaII were investigated using a DNA protection assay. This assay makes use of the fact that DNA methyltransferase-catalyzed modifications of nucleobases within the recognition sequence of restriction endonucleases can protect the DNA against fragmentation of these enzymes. DNA containing unmodified target sites of a restriction endonuclease is readily fragmented by the restriction endonuclease, whereas covalent modification of the target sites blocks the DNA cleavage. Occurrence of fragmentation is then analyzed by agarose gel electrophoresis.

A 618 bp fragment of plasmid pUC18 (pUC-618), which contains a single target site for M.HhaI, 2 sites for HpaII and 32 sites for M.SssI, was used as the DNA substrate. pUC-618 was prepared by PCR amplification of the pUC19 template (Fermentas Life Sciences) using Dir (5'-AACGTTGTTGC-CATTGCTAC) (SEQ ID No:11) and Rev (5'-GCTCAT-GAGACAATAACCCTGA) (SEQ ID No:12) primers and Taq DNA Polymerase (Fermentas Life Sciences). The PCR fragment was purified by Sephacryl S-400 (GE Healthcare) following the precipitation by ethanol.

hmC modification at the GCGC target site was introduced by treatment of 100 nM pUC-618 with 50 nM M.HhaI in buffer (50 mM MOPS, 50 mM MES pH 7.0, 1 mM $Na_2EDTA$, 15 mM NaCl, 0.2 mg/ml bovine serum albumin, 5% glycerol) with 13 mM formaldehyde for 1 hour at room temperature. 5-hydroxyethylcytosine (heC) modification at the GCGC target site was introduced by treatment of 100 nM pUC-618 with 50 nM M.HhaI with 800 mM acetaldehyde for 1 hour at room temperature as above. hmC modification at the CG target sites was introduced by treatment of 200 nM pUC-618 with 1200 nM M.SssI (Q142A/N370A) and 13 mM formaldehyde for 1 hour at room temperature as described above. hmC modification at the target CCGG sites was introduced by treatment of 200 nM pUC-618 with 2000 nM M.HpaII and 13 mM formaldehyde for 1 hour at room temperature as described above. Reactions were stopped by heating at 75° C. for 20 min. DNA was precipitated by 3 volumes of ethanol and washed ones by 75% of ethanol. Modification removal reactions were performed by incubating a duplex oligodeoxyribonucleotides with a cognate DNA methyltransferase for 2-5 hours at 37° C. in buffer (10 mM Tris-HCl pH 7.4, 50 mM NaCl, 0.5 mM $Na_2EDTA$ 0.2 mg/ml bovine serum albumin, 5% glycerol).

DNA cleavage with restriction endonucleases was performed according to manufacturer's recommendations (Fermentas Life Sciences). Samples were supplemented with ⅙ of 6× Loading Dye Solution and analyzed by 2% agarose gel electrophoresis.

Fluorescent labeling of DNA fragments was achieved by treatment of hmC-containing pUC-618 fragment (13 µL, 0.2 µM) with 25 mM 1,4 dithiothreitol in the presence of M.HhaI (1 µM) or M.SssI (6.5 µM) for 1 hour at room temperature. DNA was then purified using Qiagen Nucleotide Removal Kit and treated with 1 mM Oregon Green 488 maleimide (Invitrogen) (dissolved in dimethylformamide, Fluka) for 12 hour at room temperature in the dark in buffer (20 µL, 100 mM Tris-HCl pH 7.4, 5 mM TCEP). DNA was purified with Nucleotide Removal Kit (Qiagen) and analyzed by 2% agarose gel electrophoresis (10 V/cm) in the absence of ethidium bromide. Gels were first scanned with a Fuji FLA-5100 imaging system using a 473 nm laser and then inspected in a UV-imager after staining with ethidium bromide.

Example 7

Sequence-specific modification of a 618 bp hmC-containing DNA fragment in the presence of M.HhaI.

Figure 4:
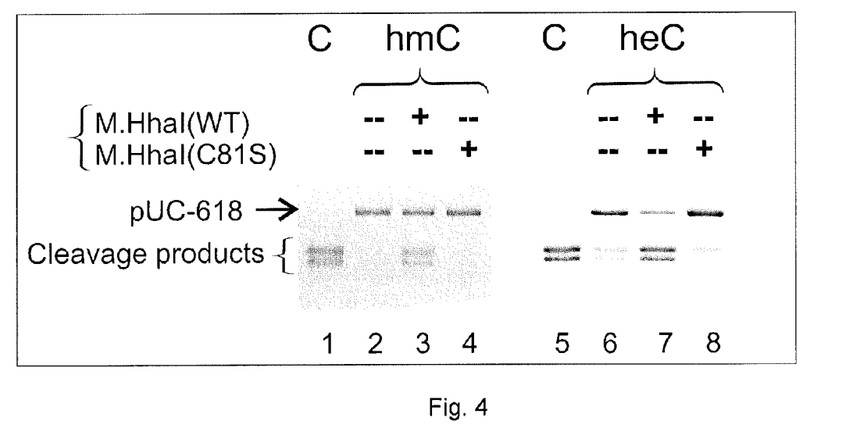
FIG. 4: Restriction endonuclease analysis of methyltransferase-directed modification of a 618 bp 5-hydroxylalkylcytosine-containing DNA fragment. The DNA fragment (100 nM) containing hmC (left panel) or heC (right panel) residues at the target GCGC site was incubated with M.HhaI (wild type or C81S mutant as shown) for 2 hours at 37° C. Modified DNAs were fragmented with a restriction endonuclease R.Hin6I and analyzed by agarose gel electrophoresis.

FIG. 4 (lanes 1-4) shows that the hmC modification makes the pUC-618 fragment resistant to R.Hin6I (lanes 1 and 2). Treatment with wild type M.HhaI renders the GCGC site largely cleavable with R.Hin6I (lane 3), however treatment with the catalytically impaired mutant C81S of M.HhaI—does not (lane 4). Thus catalytic action of M.HhaI leads to efficient removal of 5-hydroxymethyl groups from the GCGC target site in a DNA fragment.

Example 8

Sequence-specific modification of a 618 bp 5-hydroxyethylcytosine-containing DNA fragment in the presence of M.HhaI.

FIG. 4 (lanes 5-8) shows that the heC modification makes the pUC-618 fragment resistant to R.Hin6I cleavage (compare lanes 5 and 6). Treatment with wild type M.HhaI renders the GCGC site largely cleavable with R.Hin6I, (lane 7), however treatment with the catalytically impaired mutant C81S of M.HhaI—does not (lane 8). Thus catalytic action of M.HhaI leads to removal of 5-hydroxyethyl groups from the GCGC target site in a DNA fragment.

Example 9

Sequence-specific modification of a 618 bp hmC-containing DNA fragment in the presence of M.SssI.

Figure 5:
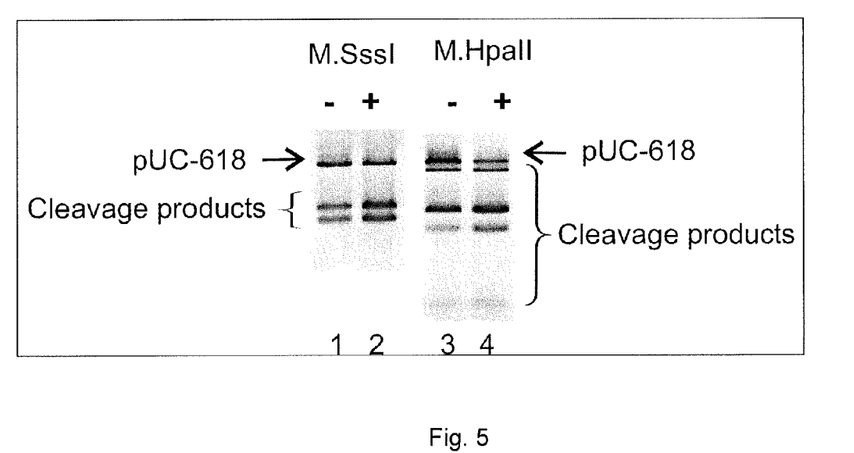
FIG. 5: Restriction endonuclease analysis of methyltransferase-directed modification of a 618 bp 5-hydroxylalkylcytosine-containing DNA fragment. The DNA fragment (100 nM) containing hmC residues at the target CG sites was incubated with M.SssI (lanes 1, 2) or HpaII (lanes 3, 4) for 2 hours at 37° C. MTase treated DNAs (lanes 2 and 4) and untreated controls (lanes 1 and 3) were fragmented with a restriction endonuclease R.Hin6I (lanes 1, 2) or R.HpaII (lanes 3, 4) and analyzed by agarose gel electrophoresis.
Figure 6:
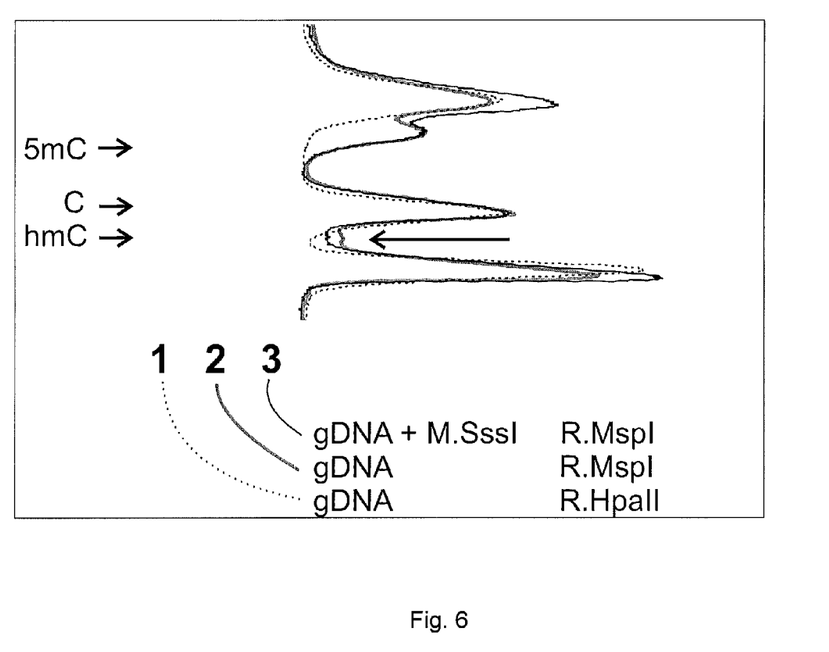
FIG. 6: TLC analysis of [$^{33}$P]-labeled 2'-deoxy-5'-mononucleotides of enzymatically fragmented genomic DNA after treatment with M.SssI. Human genomic DNA was treated with M.SssI for 2 hours at 37° C. and then cleaved with R.HpaII or R.MspI endonucleases as indicated in the right bottom corner, $^{33}$P-labeled at its 5'-ends, digested to 5'-mononucleotides and analyzed by TLC (lane 3). Control samples (lanes 1 and 2) were not treated with M.SssI, and analyzed as above. Densitometric scans of the image (lane 1—dotted line; lane 2—gray line; lane 3—solid thin line) are shown on the right. The arrow points at the position corresponding to the hmC nucleotide in the density scans.

FIG. 5 shows that the hmC modification makes the pUC-618 fragment partially resistant to R.Hin6I cleavage (lane 1). Treatment with M.SssI renders the GCGC site more cleavable with R.Hin6I (increased amount of cleavage products in lane 2). Thus action of M.SssI leads to removal of 5-hydroxymethyl groups from the GCGC target site in a DNA fragment.

Example 10

Sequence-specific modification of a 618 bp hmC-containing DNA fragment in the presence of M.HpaII.

FIG. 5 shows that the hmC modification makes the pUC-618 fragment partially resistant to R.HpaII (lane 3). Treatment with M.HpaII renders the CCGG site more cleavable with R.HpaII (increased amount of cleavage products in lane 4). Thus action of M.HpaII leads to removal of 5-hydroxymethyl groups from the CCGG target site in a DNA fragment.

Example 11

Sequence-specific conversion hmC residues to cytosines in human genomic DNA using a DNA cytosine-5 methyltransferase, M.SssI.

Figure 7:
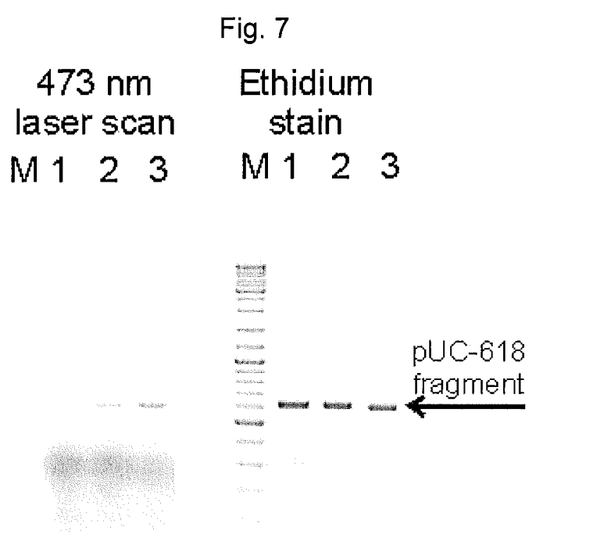

90 ng of human genomic DNA (gDNA) (isolated from post mortem human brains) was incubated in 25 µl buffer (50 mM MOPS, 50 mM MES pH 7.5, 1 mM $Na_2EDTA$, 15 mM NaCl, 0.2 mg/ml bovine serum albumin, 5% glycerol) with 1200 nM M.SssI overnight at 37° C. DNA was purified using Qiagen Nucleotide Removal Kit and fragmented with R.MspI or R.HpaII (20 u) (Fermentas Life Science) for 3 hours at 37° C. Then RnaseA (5 µg) and FastAP (0.5 u) was added and incubation was continued for one more hour. DNA again was purified with Qiagen Nucleotide Removal Kit and labeled using T4 Polynucleotide Kinase (Fermentas Life Science) and [γ-$^{33}$]ATP (Hartmann Analytic). Then DNA was precipitated with 3 volumes of ethanol and digested with Lambda Exonuclease (5 u) for one hour at 37° C. 0.5-3 µl aliquotes were spotted on TLC plates (PEI CelluloseF, 20×20 cm, Merck). TLC plates were eluted with isobutyric acid/water/conc. ammonia, (66:17:4, vol/vol/vol). Plates were dried overnight and radioactive bands were autoradiographed to an imaging plate (Fujifilm, Japan) followed by scanning with a FLA-5100 phosphoimager. Densitometric analysis of autoradiographic images was performed using MultiGauge software (Fujifilm). FIG. 7 shows a clear presence of hmC and 5mC residues at the second residue of CCGG sites (underlined) in genomic DNA from human brain—hmC and 5mC containing sites are cleaved and labeled at the second nucleotide with R.MspI (see lane 2 and corresponding black density trace on right) but are not cleaved and thus not labeled (lane 1 and dotted density trace on right) upon treatment with R.HpaII (Kriaucionis, S. & Heintz, N. *Science* published online, *doi:*10.1126/science.1169786). Treatment of genomic DNA with M.SssI reduces the amount of detectable hmC at the CCGG (lane 3 and corresponding gray trace on right). The right side arrow points at the position of hmC in the density traces. Thus the 5-hydroxymethyl group is removed from the target cytosine residues at CCGG cites in human genomic DNA in the presence of M.SssI.

Example 12

Sequence-specific fluorescent labeling of a 618 bp hmC-containing DNA fragment 1,4-dithiothreitol (DTT) in the presence of M.HhaI or M.SssI.

FIG. 7 shows that treatment with DTT in the presence of M.HhaI or M.SssI (lanes 3 and 2, respectively) followed by thiol-specific ligation with Oregon Green 488 maleimide renders the pUC-618 fragment fluorescent upon illumination with a 473 nm light. Thus labeling of a hmC-containing fragment can be achieved by DNA methyltransferase-directed coupling of DTT followed by chemo-selective ligation with a maleimide-reactive fluorescent label. A control reaction carried out without a MTase shows no visible DNA fragments in the absence of ethidium bromide staining.

In the following Examples 13 to 20 the alpha-hydroxylated residues are produced by reaction of an oligodeoxyribonucleotide with an aldehyde.

Example 13

Nucleoside composition analysis of a duplex oligodeoxyribonucleotide after sequential treatment with formaldehyde and 2-mercaptoethanol in the presence of M.HhaI.

Figure 8:
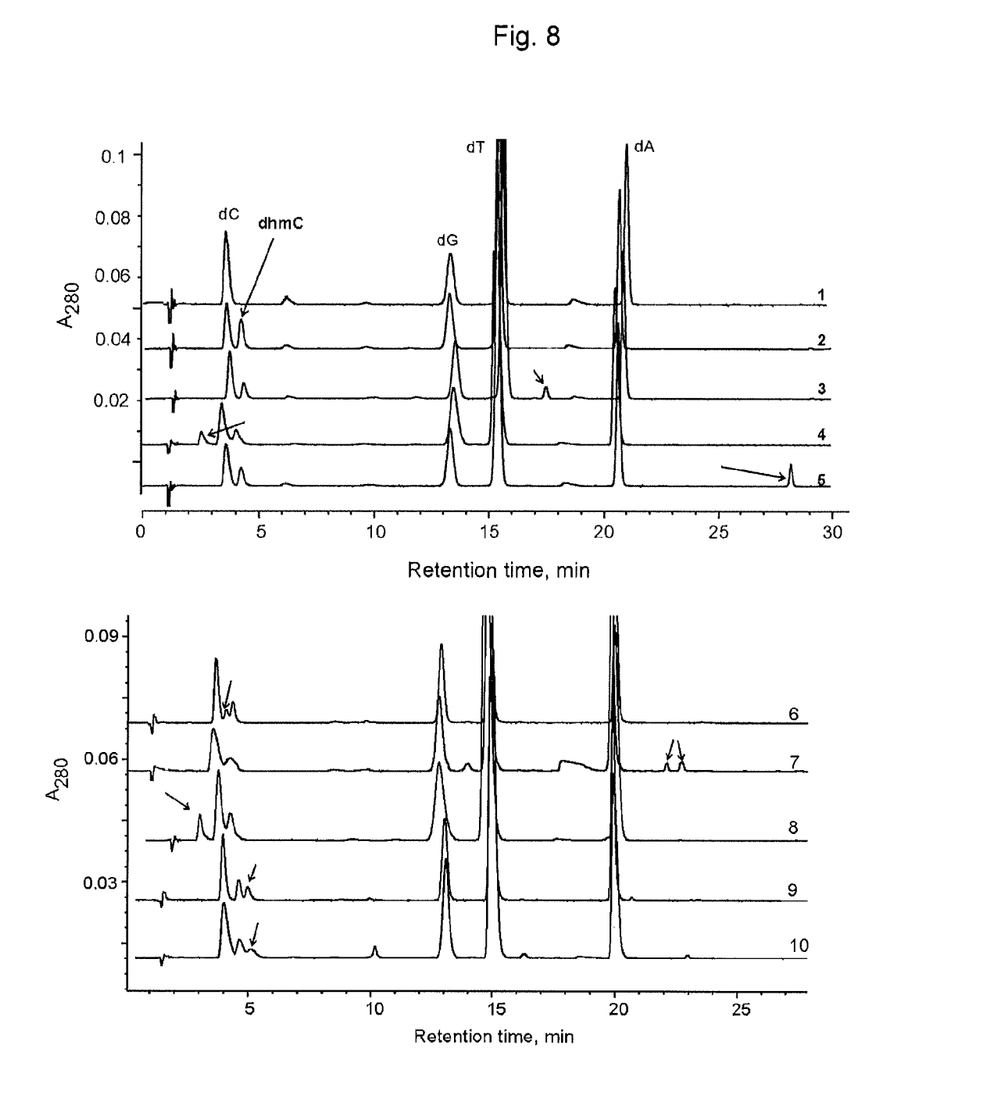
FIG. 8: Reversed-phase HPLC analysis of enzymatically fragmented duplex oligodeoxynucleotides obtained after treatment with M.HhaI, compound (I) and compound (II). 13 μM DNA duplex I:II was incubated, in the presence of 15 μM M.HhaI, with 13 mM formaldehyde for 40 min (trace 2) and then adding compound (II) to a final concentration of 300 mM 2-mercaptoethanol (trace 3), 50 mM L-cysteine (trace 4), 400 μM 5'-deoxy-5'-thioadenosine (trace 5), 12 mM cysteamine (trace 6), 50 mM dithiothreitol (trace 7), 1 mM selenocysteine (trace 8), 1.2 mM selenocysteamine (trace 9) or 50 mM hydroxylamine (trace 10) and incubating for 1 hour at room temperature. Control reaction (trace 1) lacked M.HhaI. The HPLC elution buffer A was 20 mM ammonium acetate pH 5.5. Arrows point at peaks corresponding to the new modification products.

HPLC analysis of nucleoside composition of the modified duplex oligodeoxyribonucleotide (I:II) treated with 13 mM formaldehyde (R=H) and 300 mM 2-mercaptoethanol (Q=S; LX=CH$_2$CH$_2$OH) revealed in addition to the natural nucleosides dC, dG, dT and dA two new products: one with the retention time of 5-hydroxymethyl-2'-deoxycytidine and another with a retention time of 16.8 min (elution buffer 20 mM ammonium acetate pH 5.5). This new product was analyzed by coupled ESI-MS (m/z: 340 [M+Na]$^+$, 224 [5-(2-hydroxyethyl)thiomethylcytosine+Na]$^+$) and separately by HR-MS (m/z found: 318.1118; calculated for [M+H]+ C$_{12}$H$_{20}$N$_3$O$_5$S; 318.1119). The observed masses are in agreement with 5-(2-hydroxyethylthio)methyl-2'-deoxycytidine. Thus 2-mercaptoethanol is coupled to a 5-hydroxymethylcytosine residue in DNA by M.HhaI. See FIG. 8, trace 3.

Example 14

Nucleoside composition analysis of a duplex oligodeoxyribonucleotide after sequential treatment with formaldehyde and L-cysteine in the presence of M.HhaI.

HPLC analysis of nucleoside composition of the modified duplex oligodeoxyribonucleotide (I:II) treated with 13 mM formaldehyde (R=H) and then with 50 mM L-cysteine (Q=S; LX=CH$_2$CH(CO$_2$H)NH$_2$) in the presence of M.HhaI revealed in addition to the natural nucleosides dC, dG, dT and dA two new products: one with the retention time of 5-hydroxymethyl-2'-deoxycytidine (Example 1) and another with a retention time of 2.7 min (elution buffer 20 mM ammonium acetate pH 5.5). This new products was analyzed by HR-MS (m/z found: 361.1176; calculated for [M+H]+C$_{13}$H$_{21}$N$_4$O$_6$S: 361.1176). The observed mass is in agreement with 5-(S-cysteinyl)methyl-2'-deoxycytidine. Thus L-cysteine is coupled to a 5-hydroxymethylcytosine residue in DNA by M.HhaI. See FIG. 8, trace 4.

Example 15

Nucleoside composition analysis of a duplex oligodeoxyribonucleotide after sequential treatment with formaldehyde and 5'-thio-5'-deoxyadenosine in the presence of M.HhaI.

HPLC analysis of nucleoside composition of the modified duplex oligodeoxyribonucleotide (I:II) treated with 13 mM formaldehyde (R=H) and then with 400 μM 5'-thio-5'-deoxyadenosine (Q=S; LX=5'-deoxyadenosine) in the presence of M.HhaI revealed in addition to the natural nucleosides dC, dG, dT and dA two new products: one with the retention time of 5-hydroxymethyl-2'-deoxycytidine (Example 1) and another with a retention time of 27.5 min (elution buffer 20 mM ammonium acetate pH 5.5).

This new product was analyzed by coupled ESI-MS (m/z: 545 [M+Na]+, 429 [5-(5'-denosyl)thiomethyl-2'-deoxycytidine+Na]+) and separately by HR-MS (m/z found: 523.1718; calculated for [M+H]+C$_{20}$H$_{27}$N$_8$O$_7$S: 523.1718). The observed masses are in agreement with 5-(5'-adenosyl)thiomethyl-2'-deoxycytidine. Thus 5'-thio-5'-deoxyadenosine is coupled to a 5-hydroxymethylcytosine residue in DNA by M.HhaI. See FIG. 8, trace 5.

Example 16

Nucleoside composition analysis of a duplex oligodeoxyribonucleotide after sequential treatment with formaldehyde and cysteamine in the presence of M.HhaI.

HPLC analysis of nucleoside composition of the modified duplex oligodeoxyribonucleotide (I:II) treated with 13 mM formaldehyde (R=H) and then with 12 mM cysteamine (Q=S; LX=CH$_2$CH$_2$NH$_2$) in the presence of M.HhaI revealed in addition to the natural nucleosides dC, dG, dT and dA two new products: one with the retention time of 5-hydroxymethyl-2'-deoxycytidine (Example 1) and another with a retention time of 4.0 min (elution buffer 20 mM ammonium acetate pH 5.5).

This new product was analyzed by coupled ESI-MS (m/z: 339 [M+Na]+, 223 [5-(2-aminoethyl)thiomethylcytosine+Na]+). The observed masses are in agreement with 5-(2-aminoethyl)thiomethyl-2'-deoxycytidine. Thus cysteamine is coupled to a 5-hydroxymethylcytosine residue in DNA by M.HhaI. See FIG. 8, trace 6.

Example 17

Nucleoside composition analysis of a duplex oligodeoxyribonucleotide after sequential treatment with formaldehyde and 1,4-dithiothreitol (1,4-dithio-2,3-dihydroxy-butane) in the presence of M.HhaI.

HPLC analysis of nucleoside composition of the modified duplex oligodeoxyribonucleotide (I:II) treated with 13 mM formaldehyde (R=H) and then with 50 mM 1,4-dithiothreitol (Q=S; LX=CH$_2$CH(OH)CH(OH)CH$_2$SH) in the presence of M.HhaI revealed in addition to the natural nucleosides dC, dG, dT and dA two new products: one with the retention time of 5-hydroxymethyl-2'-deoxycytidine (Example 1) and another with a retention time of 22.1 min and 22.8 min (two isomers) (elution buffer 20 mM ammonium acetate pH 5.5).

This new product was analyzed by coupled ESI-MS (m/z: 416 [M+Na]+). The observed masses are in agreement with 5-(2,3-dihydroxy-4-mercaptobutyl)thiomethyl-2'-deoxycytidine. Thus 1,4-dithiothreitol is coupled to a 5-hydroxymethylcytosine residue in DNA by M.HhaI. See FIG. 8, trace 7.

Example 18

Nucleoside composition analysis of a duplex oligodeoxyribonucleotide after sequential treatment with formaldehyde and selenocysteine in the presence of M.HhaI.

HPLC analysis of nucleoside composition of the modified duplex oligodeoxyribonucleotide (I:II) treated with 13 mM formaldehyde (R=H) and then with 50 mM selenocysteine (Q=Se; LX=CH$_2$CH(CO$_2$H)NH$_2$) in the presence of M.HhaI revealed in addition to the natural nucleosides dC, dG, dT and dA two new products: one with the retention time of 5-hydroxymethyl-2'-deoxycytidine and another with a retention time of 3.1 min (elution buffer 20 mM ammonium acetate pH 5.5). This new product was analyzed by HR-MS (m/z found: 409.0621, calculated for [M+H]+ C$_{13}$H$_{21}$N$_4$O$_6$Se: 409.0621). The observed mass is in agreement with 5-(2-amino-2-carboxyethyl)selenomethyl-2'-deoxycytidine. Thus selenocysteine is coupled to a 5-hydroxymethylcytosine residue in DNA by M.HhaI. See FIG. 8, trace 8.

Example 19

Nucleoside composition analysis of a duplex oligodeoxyribonucleotide after sequential treatment with formaldehyde and selenocysteamine in the presence of M.HhaI.

HPLC analysis of nucleoside composition of the modified duplex oligodeoxyribonucleotide (I:II) treated with 13 mM formaldehyde (R=H) and then with 1,2 mM selenocysteamine (Q=Se; LX=CH$_2$CH$_2$NH$_2$) in the presence of M.HhaI revealed in addition to the natural nucleosides dC, dG, dT and dA two new products: one with the retention time of 5-hydroxymethyl-2'-deoxycytidine and another with a retention time of 5.0 min (elution buffer 20 mM ammonium acetate pH 5.5).

This new product was analyzed by coupled ESI-MS (m/z: 386 [M+Na]+). The observed masses are in agreement with 5-(2-aminoethyl)selenomethyl-2'-deoxycytidine. Thus selenocysteamine is coupled to a 5-hydroxymethylcytosine residue in DNA by M.HhaI. See FIG. 8, trace 9.

Example 20

Nucleoside composition analysis of a duplex oligodeoxyribonucleotide after sequential treatment with formaldehyde and hydroxylamine in the presence of M.HhaI.

HPLC analysis of nucleoside composition of the modified duplex oligodeoxyribonucleotide (I:II) treated with 13 mM formaldehyde (R=H) and then with 50 mM hydroxylamine (Q=NH; LX=OH) in the presence of M.HhaI revealed in addition to the natural nucleosides dC, dG, dT and dA two new products: one with the retention time of 5-hydroxymethyl-2'-deoxycytidine and another with a retention time of 5.0 min (elution buffer 20 mM ammonium acetate pH 5.5) in agreement with the formation of 5-hydroxylaminomethyl-2'-deoxycytidine. Thus hydroxylamine is coupled to a 5-hydroxymethylcytosine residue in DNA by M.HhaI. See FIG. 8, trace 10.

The invention claimed is:

1. A method for targeted conversion of a modified biomolecule, comprising
    incubating the modified biomolecule bearing a modifying moiety of formula —CH(OH)—R, wherein R is hydrogen or C$_1$-C$_{12}$-alkyl, with a cofactor-free directing methyltransferase under conditions compatible with enzymatic activity of the methyltransferase, and
    obtaining targeted conversion resulting from:
i) covalent removal of said modifying moiety at the target site; or
ii) derivatization of said modifying moiety at the target site by covalent coupling of non-cofactor nucleophilic compound(s) of general formula HQ-LX, wherein X represents a functional group or a reporter group attached via a linker L, and Q is selected from S, Se, O, N, or C.

2. The method of claim 1 wherein said biomolecule is a nucleic acid molecule, and said methyltransferase is a DNA cytosine-5 methyltransferase selected from the group consisting of M.HhaI, M.SssI, and M.HpaII or derivatives thereof.

3. The method of claim 1, wherein the modified biomolecule is a naturally or artificially modified biomolecule, and wherein R is hydrogen or —CH$_3$ and Q is S or Se.

4. The method of claim 1 further comprising directly or subsequently incorporating a reporter group suitable as a label and allowing identification of the labeled molecule among other unlabeled molecules.

5. The method of claim 4, wherein the label is selected from fluorophores, fluorescence quenchers, chromophores, affinity tags, stable paramagnetic groups, groups containing radioactive or stable rare isotopes, groups containing heavy atoms suitable for phasing X-ray diffraction data, crosslinking agents, nucleic acids cleaving groups, haptens, nanoparticles, beads and combinations thereof.

6. The method of claim 4, wherein the coupled compound or a label in a derivatized biomolecule is identified by DNA sequencing, hybridization, mass spectrometry or analysis of nucleoside composition by enzymatic fragmentation and chromatography.

7. The method of claim 1 wherein R in the modifying moiety is hydrogen.

8. The method of claim 1 wherein R in the modifying moiety is a lower alkyl.

9. The method of claim 1 wherein R in the modifying moiety is —CH$_3$.

10. The method of claim 2 wherein the nucleic acid molecule is DNA.

11. The method of claim 4 wherein the derivatized biomolecule is DNA.

* * * * *